(12) United States Patent
Stavisky et al.

(10) Patent No.: US 12,431,136 B2
(45) Date of Patent: *Sep. 30, 2025

(54) SYSTEMS AND METHODS FOR DECODING INTENDED SPEECH FROM NEURONAL ACTIVITY

(71) Applicant: The Board of Trustees of the Leland Stanford Junior University, Stanford, CA (US)

(72) Inventors: Sergey Stavisky, Davis, CA (US); Krishna V. Shenoy, Stanford, CA (US); Jaimie M. Henderson, Redwood City, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/655,158

(22) Filed: May 3, 2024

(65) Prior Publication Data
US 2025/0006190 A1 Jan. 2, 2025

Related U.S. Application Data

(63) Continuation of application No. 16/399,412, filed on Apr. 30, 2019, now Pat. No. 12,008,987.
(Continued)

(51) Int. Cl.
*G10L 15/22* (2006.01)
*A61B 5/00* (2006.01)
(Continued)

(52) U.S. Cl.
CPC ............ *G10L 15/22* (2013.01); *A61B 5/0031* (2013.01); *A61B 5/24* (2021.01); *A61B 5/686* (2013.01);
(Continued)

(58) Field of Classification Search
CPC ......... G10L 15/22; G10L 13/00; G10L 15/02; G10L 15/16; G10L 15/183; G10L 19/00;
(Continued)

(56) References Cited

U.S. PATENT DOCUMENTS 8,335,993 B1 12/2012 Tan
D684,154 S 6/2013 Schontag
(Continued)

FOREIGN PATENT DOCUMENTS

KR 20130002590 A 1/2013
KR 20150133937 A 12/2015
WO 2022006462 A1 1/2022

OTHER PUBLICATIONS

Herff, Brain-to-text: decoding spoken phases from phone representations in the brain, 2015, frontiers in Neuroscience, whole document (Year: 2015).*
(Continued)

*Primary Examiner* — Sonia L Gay
(74) *Attorney, Agent, or Firm* — KPPB LLP (57) ABSTRACT

Systems and methods for decoding indented speech from neuronal activity in accordance with embodiments of the invention are illustrated. One embodiment includes a neuronal speech system for decoding intended speech from neuronal signals includes a neuronal signal recorder implanted into a user's brain, including a multielectrode array, controller circuitry, and a communication circuitry capable of transmitting data to a neuronal signal decoder, the neuronal signal decoder located externally from the user's body, including a processor, an input/output interface, and a memory, where the memory contains a neuronal speech application that directs the processor to obtain neuronal signal data from the neuronal signal recorder, where the neuronal signal data describes neuronal activity proximal to the implanted neuronal signal recorder, decode speech fea-
(Continued)

tures from the neuronal signal data using a neuronal decoding model, construct a speech string from the decoded speech features; and output the constructed speech string via an output device.

20 Claims, 4 Drawing Sheets

Related U.S. Application Data (60) Provisional application No. 62/664,385, filed on Apr. 30, 2018.

(51) Int. Cl.
| | | |
|---|---|---|
| A61B 5/24 | (2021.01) | |
| G06N 3/08 | (2023.01) | |
| G10L 13/00 | (2006.01) | |
| G10L 15/02 | (2006.01) | |
| G10L 15/16 | (2006.01) | |
| G10L 15/183 | (2013.01) | |
| G10L 19/00 | (2013.01) | |

(52) U.S. Cl.
CPC ............ *A61B 5/7264* (2013.01); *A61B 5/741* (2013.01); *G06N 3/08* (2013.01); *G10L 13/00* (2013.01); *G10L 15/02* (2013.01); *G10L 15/16* (2013.01); *G10L 15/183* (2013.01); *G10L 19/00* (2013.01); *A61B 2562/046* (2013.01); *G10L 2015/025* (2013.01)

(58) Field of Classification Search
CPC ... G10L 2015/025; A61B 5/24; A61B 5/0031; A61B 5/686; A61B 5/7264; A61B 5/741; G96N 3/98
See application file for complete search history.

(56) References Cited

U.S. PATENT DOCUMENTS

| | | |
|---|---|---|
| 8,949,743 B2 | 2/2015 | Kida et al. |
| 9,373,088 B2 | 6/2016 | Nuyujukian et al. |
| 10,223,634 B2 | 3/2019 | Sussillo et al. |
| 10,779,746 B2 | 9/2020 | Even-Chen et al. |
| 10,949,086 B2 | 3/2021 | Even-Chen et al. |
| 11,461,618 B2 | 10/2022 | Sussillo et al. |
| 11,989,641 B2 | 5/2024 | Sussillo et al. |
| 12,008,987 B2 | 6/2024 | Stavisky et al. |
| 2003/0056278 A1 | 3/2003 | Kuo et al. |
| 2003/0105409 A1 | 6/2003 | Donoghue et al. |
| 2004/0073414 A1 | 4/2004 | Bienenstock et al. |
| 2004/0267320 A1 | 12/2004 | Taylor et al. |
| 2005/0017870 A1 | 1/2005 | Allison et al. |
| 2005/0228515 A1 | 10/2005 | Musallam et al. |
| 2006/0159195 A1 | 7/2006 | Ionescu et al. |
| 2006/0167371 A1 | 7/2006 | Flaherty et al. |
| 2006/0274060 A1 | 12/2006 | Ni et al. |
| 2009/0167706 A1 | 7/2009 | Tan et al. |
| 2010/0241993 A1 | 9/2010 | Chae |
| 2010/0274746 A1 | 10/2010 | Rickert et al. |
| 2010/0280403 A1 | 11/2010 | Erdogmus et al. |
| 2011/0092842 A1 | 4/2011 | Decaria et al. |
| 2011/0224572 A1 | 9/2011 | Gilja et al. |
| 2011/0295143 A1 | 12/2011 | Leuthardt et al. |
| 2011/0307079 A1 | 12/2011 | Oweiss et al. |
| 2012/0022391 A1 | 1/2012 | Leuthardt |
| 2012/0030696 A1 | 2/2012 | Smith |
| 2012/0130266 A1 | 5/2012 | Mathan et al. |
| 2012/0221075 A1 | 8/2012 | Bentwich |
| 2012/0242659 A1 | 9/2012 | Sun |
| 2013/0253299 A1 | 9/2013 | Weber et al. |
| 2013/0311412 A1 | 11/2013 | Lazar et al. |
| 2013/0314320 A1 | 11/2013 | Hwang et al. |
| 2014/0132519 A1 | 5/2014 | Chun |
| 2014/0194720 A1 | 7/2014 | Hua |
| 2014/0358192 A1 | 12/2014 | Wheeler Moss et al. |
| 2015/0091791 A1 | 4/2015 | Segal |
| 2015/0120777 A1 | 4/2015 | Ramos |
| 2015/0124063 A1 | 5/2015 | Woods |
| 2015/0248234 A1 | 9/2015 | Chen et al. |
| 2015/0268814 A1 | 9/2015 | Wang |
| 2015/0269336 A1 | 9/2015 | Duan et al. |
| 2015/0297106 A1 | 10/2015 | Pasley et al. |
| 2016/0048753 A1 | 2/2016 | Sussillo et al. |
| 2016/0180215 A1 | 6/2016 | Vinyals et al. |
| 2016/0224891 A1 | 8/2016 | Kao et al. |
| 2016/0299568 A1 | 10/2016 | Segal |
| 2016/0365090 A1* | 12/2016 | Nissan .................... G10L 15/19 |
| 2017/0042440 A1 | 2/2017 | Even-chen et al. |
| 2017/0108926 A1 | 4/2017 | Moon et al. |
| 2017/0139587 A1 | 5/2017 | Bostick et al. |
| 2017/0147077 A1 | 5/2017 | Park et al. |
| 2017/0344220 A1 | 11/2017 | Cook et al. |
| 2018/0101239 A1 | 4/2018 | Yin et al. |
| 2019/0021663 A1 | 1/2019 | Kesinger et al. |
| 2019/0025917 A1 | 1/2019 | Francis et al. |
| 2019/0053725 A1 | 2/2019 | Von Novak et al. |
| 2019/0205731 A1 | 7/2019 | Sussillo et al. |
| 2019/0333505 A1 | 10/2019 | Stavisky et al. |
| 2020/0057964 A1 | 2/2020 | Howard |
| 2020/0133486 A1 | 4/2020 | Even-Chen et al. |
| 2020/0187841 A1 | 6/2020 | Ayyad |
| 2021/0064135 A1 | 3/2021 | Shenoy et al. |
| 2023/0144342 A1 | 5/2023 | Sussillo et al. |

OTHER PUBLICATIONS

Choi, Future Directions for Brain-Machine Interfacing Technology, 2015, Springer Science, whole document (Year: 2015).*
Andersen et al., "Selecting the Signals for a Brain-Machine Interface", Current Opinion in Neurobiology, vol. 14, No. 6, Dec. 2004, pp. 720-726.
Anumanchipalli et al., "Intelligible Speech Synthesis from Neural Decoding of Spoken Sentences", bioRxiv, Nov. 29, 2018, 32 pgs.
Artusi et al., "Performance of a Simulated Adaptive BCI Based on Experimental Classification of Movement-Related and Error Potentials", IEEE Journal on Emerging and Selected Topics in Circuits and Systems, vol. 1, No. 4, Dec. 2011.
Bacher et al., "Neural Point-and-Click Communication by a Person With Incomplete Locked-In Syndrome", Neurorehabilitation and Neural Repair, vol. 29, No. 5, Nov. 10, 2014, pp. 462-471.
Bouchard et al., "Control of Spoken Vowel Acoustics and the Influence of Phoentic Context in Human Speech Sensorimotor Cortex", The Journal of Neuroscience, vol. 34, No. 38, Sep. 17, 2014, pp. 12662-12677.
Bouchard et al., "Functional Organization of Human Sensorimotor Cortex for Speech Articulation", HHS Public Access—Author Manuscript, 21 pgs., published in final form as Nature, vol. 495, No. 7441, Mar. 21, 2013, pp. 327-332.
Bouchard et al., "Neural Decoding of Spoken Vowels from Human Sensory-Motor Cortex with High-Density Electrocorticography", 36th Annual International Conference of the IEEE Engineering in Medicine and Biology Society, Aug. 26-30, 2014, Chicago, IL.
Breshears et al., "A Probabilistic Map of the Human Ventral Sensorimotor Cortex Using Electrical Stimulation", Journal of Neurosurgey, vol. 123, No. 2, Aug. 2015, E Publication May 15, 2015.
Brumberg et al., "Classification of Intended Phoneme Production from Chronic Intracortical Microelectrode Recordings in Speech-Motor Cortex", Frontiers in Neuroscience, vol. 5, May 12, 2011, 2 pgs.
Chakrabarti et al., "Progress in Speech Decoding from the Electrocorticogram", Biomedical Engineering Letters, vol. 5, No. 1, Mar. 2015, pp. 10-21.
Chan et al., "Decoding Word and Category-Specific Spatiotemporal Representations from MEG and EEG", NIH Public Access—Author Manuscript, 24 pgs., published in final form as Neuroimage, vol. 54, No. 4, Feb. 14, 2011, pp. 3028-3039.

(56) References Cited

OTHER PUBLICATIONS

Chan et al., "Speech-Specific Tuning of Neurons in Human Superior Temporal Gyrus", Cerebral Cortex, vol. 24, No. 10, Oct. 2014, pp. 2679-2693.
Chavarriaga et al., "Errare machinale est: the use of error-related potentials in brain-machine interfaces", Frontiers in Neuroscience, vol. 8, Article 208 (2014).
Chestek et al., "Long-term stability of neural prosthetic control signals from silicon cortical arrays in rhesus macaque motor cortex", Journal of neural engineering, 8(4):045005, Jul. 2011.
Cheung et al., "The Auditory Representation of Speech Sounds in Human Motor Cortex", eLife, 2019, 19 pgs.
Churchland et al., "Techniques for Extracting Single-Trial Activity Patterns from Large-Scale Neural Recordings", Current Opinion in Neurobiology, vol. 17, No. 5, Oct. 2007, pp. 609-618.
Churchland et al., "Techniques for extracting single-trial activity patterns from large-scale neural recordings.", Current opinion in neurobiology, 17(5):609-618, Oct. 2007.
Collinger et al., "7 degree-of-freedom neuroprosthetic control by an individual with tetraplegia", NIH Public Access—Author Manuscript, 17 pgs., published in final form as "High-Performance Neuroprosthetic Control by an Individual with Tetraplegia", The Lancet, vol. 381, No. 9866, Feb. 16, 2013, 17 pgs.
Creutzfeldt et al., "Neuronal Activity in the Human Lateral Temporal Lobe: I. Responses to Speech", Experimental Brain Research, vol. 77, No. 3, 1989, pp. 451-475.
Cunningham et al., "A closed-loop human simulator for investigating the role of feedback control in brain-machine interfaces", Journal of neurophysiology, 105(4):1932-1949, Apr. 2011.
Daffau et al., "The Role of Dominant Premotor Cortex in Language: A Study Using Intraoperative Functional Mapping in Awake Patients", Neuroimage, vol. 20, No. 4, Dec. 2003, pp. 1903-1914.
Einevoll et al., "Modelling and Analysis of Local Field Potentials for Studying the Function of Cortical Circuits", Nature Review Neuroscience, vol. 14, No. 11, Nov. 2013, pp. 770-785.
Even-Chen et al., "Auto-Deleting Brain Machine Interface: Error Detection Using Spiking Neural Activity in the Motor Cortex", 37th Annual International Conference of the IEEE Engineering in Medicine and Biology Society, Aug. 25-29, 2015, Milan, Italy, 5 pgs.
Even-Chen et al., "Feasibility of Automatic Error Detect-and-Undo System in Human Intracortical Brain-Computer Interfaces", IEEE Transactions on Biomedical Engineering, vol. 65, No. 8, Aug. 2018, pp. 1771-1784.
Fan et al., "Intention Estimation in Brain-Machine Interfaces", NIH Public Access—Author Manuscript, 28 pgs., published in final form as Journal Neural Engineering, vol. 11, No. 1, Feb. 2014.
Ferrez et al., "EEG-Based Brain-Computer Interaction: Improved Accuracy by Automatic Single-Trial Error Detection", Advances in Neural Information Processing Systems 20, 2007, 8 pgs.
Ferrez et al., "Simultaneous Real-Time Detection of Motor Imagery and Error-Related Potentials for Improved BCI Accuracy", In proceedings of the 4th Inti. Brain-Computer Interface Workshop and Training Course (2008).
Gilja et al., "A High-Performance Neural Prosthesis Enabled by Control Algorithm Design", Nature Neuroscience, vol. 15, No. 12, Dec. 2012, Published Online: Nov. 18, 2012, pp. 1752-1757.
Golub et al., "Internal Models Engaged by Brain-Computer Interface Control", NIH Public Access—Author Manuscript, 11 pgs., published in final form as 34th Annual International Conference of the IEEE EMBS, vol. 2012, 2012, pp. 1327-1330.
Guenther et al., "A Wireless Brain-Machine Interface for Real-Time Speech Synthesis", PLoS One, vol. 4, No. 12, Dec. 9, 2009, 11 pgs.
Herff et al., "Automatic Speech Recognition from Neural Signals: A Focused Review", Front Neuroscience, vol. 10, No. 429, Sep. 2016, pp. 1-7.
Herff et al., "Brain-to-text: decoding spoken phrases from phone representations in the brain", Frontiers in Neuroscience, Jun. 12, 2015 vol. 9, No. 217, 11 pgs.

Hill et al., "Recording Human Electrocorticographic (ECoG) Signals for Neuroscientific Research and Real-time Functional Cortical Mapping", Journal of Visualized Experiments, 2012, vol. 64.
Hochberg et al., "Neuronal ensemble control of prosthetic devices by a human with tetraplegia", Nature, vol. 442, No. 7099, Jul. 13, 2006, pp. 164-171.
Homer et al., "Sensors and Decoding for Intracortical Brain Computer Interfaces", Annual Review of Biomedical Engineering, vol. 15, Jul. 2013.
Jozefowicz et al., "Exploring the Limits of Language Modeling", arXiv:1602.02410v2, Feb. 11, 2016, 11 pgs.
Kao et al., "Information Systems Opportunities in Brain-Machine Interface Decoders", Proceedings of the IEEE, vol. 102, No. 5, May 2014, 17 pgs.
Kellis et al., "Decoding Spoken Words Using Local Field Potentials Recorded from the Cortical Surface", NIH Public Access—Author Manuscript, 20 pgs., published in final form as Journal of Neural Engineering, vol. 7, No. 5, Oct. 2010.
Kim et al., "Neural control of computer cursor velocity by decoding motor cortical spiking activity in humans with tetraplegia", Journal of neural engineering, 5(4):455-476, Dec. 2008.
Leuthardt et al., "Using the Electrocorticographic Speech Network to Control a Brain-Computer Interface in Humans", NIH Public Access—Author Manuscript, 22 pgs., published in final form as Journal of Neural Engineering, vol. 8, No. 3, Jun. 2011.
Llera, , "Adaptive Classification on Brain-Computer Interfaces Using Reinforcement Signals", Neural Computation, 2012.
Lotte et al., "Electrocorticographic Representations of Segmental Features in Continuous Speech", Frontiers in Human Neuroscience, vol. 9, Feb. 24, 2015, 13 pgs.
Malik et al., "Efficient Decoding with Stead-State Kalman Filter in Neural Interface Systems", NIH Public Access—Author Manuscript, 25 pgs., published in final form as IEEE Trans Neural System Rehabilitation Engineering, vol. 19, No. 1, Feb. 2011, pp. 25-34.
Martin et al., "Decoding Spectrotemporal Features of Overt and Covert Speech from the Human Cortex", Front Neuroengineering, vol. 7, May 27, 2014, 15 pgs.
Meister et al., "Motor Cortex Hand Area and Speech: Implications for the Development of Language", Neuopsychologia, vol. 41, No. 4, 2003, pp. 401-406.
Mugler et al., "Direct Classification of all American English Phonemes Using Signals from Functional Speech Motor Cortex", NIH Public Access—Author Manuscript, 16 pgs., published in final form as Journal of Neural Engineering, vol. 11, No. 3, Jun. 2014.
Mulliken et al., "Decoding Trajectories from Posterior Parietal Cortex Ensembles", Journal of Neuroscience, vol. 28, No. 48, Nov. 26, 2008, pp. 12913-12926.
Nguyen et al., "Inferring Imagined Speech using EEG Signals: A New Approach Using Riemannian Manifold Features", Journal of Neural Engineering, vol. 15, No. 1, 2017.
Nuyujukian et al., "A High-Performance Keyboard Neural Prosthesis Enabled by Task Optimization", IEEE Transactions on Biomedical Engineering, vol. 62, No. 1, Jan. 2015, pp. 21-29.
Nuyujukian et al., "A High-Performance Keyboard Neural Prosthesis Enabled by Task Optimization", IEEE Transactions on Biomedical Engineering, vol. 62, No. 1, Sep. 4, 2014.
Nuyujukian et al., "Monkey Models for Brain-Machine Interfaces: The Need for Maintaining Diversity", 33rd Annual International Conference of the IEEE EMBS, Aug. 30-Sep. 3, 2011, Boston, Massachusetts, 5 pgs.
Orsborn et al., "Closed-Loop Decoder Adaptation Shapes Neural Plasticity for Skillful Neuroprosthetic Control", Neuron, vol. 82, No. 6, Jun. 2014, pp. 1380-1393.
Pandarinath et al., "High performance communication by people with paralysis using an intracortical brain-computer interface", Elife, vol. 6, Feb. 21, 2017, 27 pgs.
Ramsey et al., "Decoding Spoken Phonemes from Sensorimotor Cortex with High-Density ECoG Grids", Neuroimage, Oct. 15, 2018, E Publication Oct. 7, 2017.
Ryu et al., "Human cortical prostheses: lost in translation?", Neurosurgical Focus, 2009.
Sahin et al., "Sequential Processing of Lexical, Grammatical, and Phonological Information within Broca's Area", NIH Public Access—

(56) References Cited

OTHER PUBLICATIONS

Author Manuscript, 11 pgs., published in final form as Science, vol. 326, No. 5951, Oct. 16, 2009, pp. 445-449.
Sanchez et al., "Interpreting Spatial and Temporal Neural Activity Through a Recurrent Neural Network Brain-Machine Interface", IEEE Transactions on Neural Systems and Rehabilitation Engineering, Jun. 2005, vol. 13, No. 2.
Santhanam et al., "A high-performance brain-computer interface", Nature, vol. 442, No. 7099, Jul. 13, 2006, pp. 195-198.
Schmidt et al., "Online detection of error-related potentials boosts the performance of mental typewriters", BMC Neurosci. 13:19 (2012).
Shadmehr et al., "Error Correction, Sensory Prediction, and Adaptation in Motor Control", Annu Rev Neuroscience, vol. 33, Jan. 2010, pp. 89-108.
Shenoy et al., "Combining Decoder Design and Neural Adaptation in Brain-Machine Interfaces", Neuron, vol. 84, No. 4, Nov. 19, 2014, 16 pgs.
Shenoy et al., "Cortical Control of Arm Movements: A Dynamical Systems Perspective", Annual Rev Neuroscience, vol. 36, Jul. 8, 2013, E-Publication May 29, 2013.
Simonyan et al., "New Developments in Understanding the Complexity of Human Speech Production", The Journal of Neuroscience, vol. 36, No. 45, Nov. 9, 2016, pp. 11440-11448.
Spuler et al., "Error-related potentials during continuous feedback: using EEG to detect errors of different type and severity", Frontiers in Human Neuroscience, vol. 9, Article 155 (2015).
Stavisky et al., "A High Performing Brain-Machine Interface Driven by Low-Frequency Local Field Potentials Alone and Together with Spikes", HHS Public Access—Author Manuscript, 36 pgs., published in final form as Journal of Neural Engineering, vol. 12, No. 3, Jun. 2015.
Stavisky et al., "Decoding Speech from Intracortical Multielectrode Arrays in Dorsal "Arm/Hand Areas" of Human Motor Cortex", Annual Conference of the IEEE Engineering in Medicine and Biology Society, Jul. 2018, 5 pgs.
Subasi et al., "EEG signal classification using PCA, ICA, LDA and support vector machines", Expert Systems with Applications, 2010, vol. 37, pp. 8659-8666.
Suppes et al., "Brain Wave Recognition of Words", Proceedings of the National Academy of Sciences, vol. 94, No. 26, Dec. 23, 1997, 5 pgs.
Sussillo et al., "A recurrent neural network for closed-loop intracortical brain-machine interface decoders", Journal of neural engineering 9.2: 026027 Published Mar. 19, 2012.
Sussillo et al., "Making brain-machine interfaces robust to future neural variability", Nature Communications, Published Dec. 13, 2016, 12 pgs.
Sutskever et al., "Generating Text with Recurrent Neural Networks", Proceedings of the 28th International Conference on Machine Learning (ICML-11). 2011.
Tankus et al., "Structured Neuronal Encoding and Decoding of Human Speech Features", HHS Public Access—Author Manuscript, 11 pgs., published in final form as Nature Communications, vol. 3, 2012.
Towle et al., "ECoG Gamma Activity During a Language Task: Differentiating Expressive and Receptive Speech Areas", Brain, vol. 131, No. 8, Aug. 2008, pp. 2013-2027.
Trautmann et al., "Accurate Estimation of Neural Population Dynamics Without Spike Sorting", Neuron, vol. 103, No. 2, Jul. 17, 2019, 42 pgs.
Vainio et al., "Shared Processing of Planning Articulatory Gestures and Grasping", Experimental Brain Research, vol. 232, No. 7, Jul. 2014, pp. 2359-2368.
Waldert et al., "Influence of Spiking Activity on Cortical Local Field Potentials", The Journal of Physiology, vol. 21, Nov. 1, 2013, E Publication Aug. 27, 2013, pp. 5291-5303.
Willett et al., "Improving Brain-Machine Interface Performing by Decoding Intended Future Movements", NIH Public Access—Author Manuscript, 27 pgs., published in final form as J. Neural Engineering, vol. 10, No. 2, Apr. 2013, E-Publication Feb. 21, 2013.
Wise et al., "Premotor and Parietal Cortex: Corticocortical Connectivity and Combinatorial Computations", Annu Rev Neuroscience, vol. 20, 1997, pp. 25-42.
Yang et al., "Sensorimotor Experience and Verb-Category Mapping in Human Sensory, Motor and Parietal Neurons", HHS Public Access—Author Manuscript, 29 pgs., published in final form as Cortex, vol. 92, Jul. 2017, pp. 304-319.
International Search Report and Written Opinion for International Application No. PCT/US2021/040192, Search completed Nov. 6, 2021, Mailed Dec. 9, 2021, 21 Pgs.
"Advanced Biosignal Acquisition, Processing and Analysis", g.tec medical engineering GmbH, product catalogue, 2016, 116 pgs.
"User-ready brain-computer interface applications", intendiX, g.tec product catalogue, 2016, pp. 96-97.
Ajiboye et al., "Restoration of reaching and grasping movements through brain-controlled muscle stimulation in a person with tetraplegia: a proof-of-concept demonstration", Lancet, vol. 389, No. 10081, May 6, 2017, Electronic Publication: Mar. 28, 2017, pp. 1821-1830.
Barrero et al., "Evaluation of Text Entry Methods for Interactive Digital Television Applications with Devices Alternative to Conventional Remote Controls", International Journal of Human-Computer Interaction, vol. 32, No. 10, 2016, pp. 765-776.
Bocquelet, "Toward a Brain-Computer Interface for Speech Restoration", Electronics. Universite Grenoble Alpes, 2017. English. ffNNT: 2017GREAS008ff. fftel-01693270f, 232 pgs.
Bouton et al., "Restoring cortical control of functional movement in a human with quadriplegia", Nature, vol. 533, No. 7602, May 12, 2016, pp. 247-250.
Branco et al., "Decoding Hand Gestured from Primary Somatosensory Cortex Using High-Density ECoG", Neuroimage, Feb. 15, 2017, vol. 147, pp. 130-142.
Brumberg et al., "Brain-Computer Interfaces for Speech Communication", Speech Communication, Apr. 1, 2010, vol. 52, Issue 4, pp. 367-369.
Carmena et al., "Learning to Control a Brain-Machine Interface for Reaching and Grasping by Primates", PLoS Biology, vol. 1, No. 2, Nov. 2003, Electronic Publication: Oct. 13, 2003, pp. 193-208.
Cecotti et al., "One step beyond rows and columns flashes in the P300 speller: a theoretical description", International Journal of Bioelectromagnetism, vol. 13, No. 1, 2010, pp. 39-41.
Chen et al., "High-Speed Spelling with a Noninvasive Brain-Computer Interface", Proceedings of the National Acad Sci, 112, 2015, pp. E6058-E6067.
Christie et al., "Comparision of Spike Soring and Thresholding of Woltage Waveforms for Intracortical Brain-Machine Interface Performance", Journal of Neural Engineering, 12, 2014, 016009, 16 pgs.
Chun et al., "BCI based Hybrid Interface for 3D Object Control in Virtual Reality", IEEE International Conference on Brain-Computer Interface, Feb. 22-24, 2016, 4pgs.
Collinger et al., "Functional priorities, assistive technology, and brain-computer interfaces after spinal cord injury", Journal of Rehabilitation Research and Development, vol. 50, No. 2, 2013, pp. 145-160.
Corley et al., "Brain-Computer Interface Virtual Keyboard for Accessibility", University of Alabama: Department of Computer Science, Jun. 2012, 6pgs.
Downey et al., "Blending of brain-machine interface and vision-guided autonomous robotics improves neuroprosthetic arm performance during grasping", Journal of NeuroEngineering and Rehabilitation, vol. 13, No. 28, Mar. 18, 2016, 12 pgs.
Ethier et al., "Restoration of grasp following paralysis through brain-controlled stimulation of muscles", Nature, vol. 485, No. 7398, May 17, 2012, pp. 368-371.
Even-Chen et al., "Augmenting intracortical brain-machine interface with neurally driven error detectors", Journal of Neural Engineering, vol. 14, No. 6, Nov. 10, 2017, 16 pgs.
Fowler et al., "Improved inference and autotyping in EEG-based BCI typing systems", Proceedings of the ACM SIGACCESS Conference on Computers and Accessibility, Oct. 21-23, 2013, 8pgs.

(56) References Cited

OTHER PUBLICATIONS

Ganguly et al., "Emergence of a Stable Cortical Map for Neuroprosthetic Control", PLoS Biology, vol. 7, No. 7, Jul. 21, 2009, e1000153, 13 pgs.

Gilja et al., "Clinical Translation of a High Performance Neural Prosthesis", Nature America, whole document, 2015.

Hochberg et al., "Reach and grasp by people with tetraplegia using a neurally controlled robotic arm", Nature, vol. 485, No. 7398, May 17, 2012, pp. 372-375.

Hoggan et al., "Investigating the Effectiveness of Tactile Feedback for Mobile Touchscreens", Proceedings of the SIGCHI Conference on Human Factors in Computing Systems, Florence, Italy, Apr. 5-10, 2008, pp. 1573-1582.

Jarosiewicz et al., "Virtual typing by people with tetraplegia using a self-calibrating intracortical brain-computer interface", Science Translational Medicine, 7, 2015.

Jarosiewicz et al., "Virtual typing by people with tetraplegia using a self-calibrating intracortical brain-computer interface", Science Translational Medicine, vol. 7, No. 313, Nov. 11, 2015, 11 pgs.

Judy et al., "Data Reduction Techniques in Neural Recording Microsystems", Advances in Bioengineering, 2015, p. 291-298.

Kao et al., "A High-Performance Neural Prosthesis Incorporating Discrete State Selection With Hidden Markov Models", IEEE Transactions on Biomedical Engineering, vol. 64, No. 4, Apr. 2017, pp. 935-945.

Kao et al., "Single-trial dynamics of motor cortex and their applications to brain-machine interfaces", Nature Communications, vol. 6, No. 7759, Jul. 29, 2015, 12 pgs.

Krusienski et al., "Control of a Visual Keyboard Using an Electrocorticographic Brain-Computer Interface", Neurorehabilitation and Neural Repair, vol. 25, No. 4, May 2011, pp. 323-331, doi:10.1177/1545968310382425.

Lau et al., "A Special Virtual Keyboard for Disabled Computer Users", Proceedings of the International MultiConference of Engineers and Computer Scientists, Mar. 15-17, 2017, 6pgs.

Lopez et al., "Text entry with the Apple iPhone and the Nintendo Wii", Proceedings of the Twenty-Seventh Annual SIGCHI Conference on Human Factors in Computing Systems, Boston, USA, Apr. 4-9, 2008, 8 pgs.

Mackenzie et al., "Text Entry for Mobile Computing: Models and Methods, Theory and Practice", Human-Computer Interaction, vol. 17, No. 2-3: Text Entry for Mobile Computing, Sep. 2002, pp. 147-198.

Makin, "Brain-Computer Interface Allows Speediest Typing to Date", Scientific American, Feb. 21, 2017, 5pgs.

Makin et al., "Machine Translation of Cortical Activity to Text with an Encoder-Decoder Framework", Nature Neuroscience 1-8, 2020, DOI: 10.1038/s41593-020-0608-8, pp. 1-22.

Mayaud et al., "Robust Brain-computer interface for virtual Keyboard (RoBIK): project results", IRBM, Elsevier Masson, vol. 34, No. 2, 2013, pp. 131-138.

Moritz et al., "Direct control of paralysed muscles by cortical neurons", Nature, vol. 456, No. 7222, Dec. 4, 2008, pp. 639-642.

Musallam et al., "Cognitive Control Signals for Neural Prosthetics", Science, vol. 305, No. 5681, Jul. 9, 2004, pp. 258-262.

Noorzadeh et al., "Beyond 2D for brain-computer interfaces: two 3D extensions of the P300-speller", Proceedings of the IEEE International Conference on Acoustics, Speech, and Signal Processing, May 2014, pp. 5940-5944.

Nuyujukian et al., "A Nonhuman Primate Brain-Computer Typing Interface", Proceedings of the IEEE, vol. 105, No. 1, Jan. 2017, pp. 66-72.

Orhan et al., "RSVP Keyboard: An EEG Based Typing Interface", Proceedings of the IEEE International Conference of Acoustics Speech and Signal Processing, Sep. 12, 2013, 11pgs.

Paninski et al., "Neural data science: accelerating the experiment-analysis-theory cycle in large-scale neuroscience", Current Opinion in Neurobiology, vol. 50, Jun. 2018, pp. 232-241.

Serruya et al., "Brain-machine interface: Instant neural control of a movement signal", Nature, vol. 416, No. 6877, Mar. 14, 2002, pp. 141-142.

Smith et al., "Optimizing Touchscreen Keyboards for Gesture Typing", Proceedings of the 33rd Annual ACM Conference on Human Factors in Computing Systems, Seoul, Korea, Apr. 18-23, 2015, pp. 3365-3374.

Taylor et al., "Direct Cortical Control of 3D Neuroprosthetic Devices", Science, vol. 296, No. 5574, Jun. 7, 2002, pp. 1829-1832.

Velliste et al., "Cortical control of a prosthetic arm for self-feeding", Nature, vol. 453, No. 7198, Jun. 19, 2008, pp. 1098-1101.

Venkatagiri, "Clinical measurement of rate of reading and discourse in young adults", Journal of Fluency Disorders, vol. 24, No. 3, Sep. 1999, pp. 209-226.

Wang et al., "Corrigendum: Long-Term Decoding Stability of Local Field Potentials from Silicon Arrays in Primate Motor Cortex During a 2D Center Out Task", J. Neural Eng. 11 036009, 2014, p. 1-4.

Wang et al., "P300 Brain-Computer Interface Design for Communication and Control Applications", Proceedings of the IEEE International Conference of Engineering in Medicine and Biology, Sep. 1-4, 2005, 4pgs.

Willett et al., "Hand Knob Area of Premotor Cortex Represents the Whole Body in a Compositional Way", Cell, vol. 181, No. 2, 2020, pp. 396-409.e26, DOI: 10.1016/j.cell.2020.02.043.

Yousry et al., "Localization of the motor hand area to a knob on the precentral gyrus. A new landmark", Brain, 120, 1997, pp. 141-157.

Zhang et al., "Converting Your Thoughts to Texts: Enabling Brain Typing via Deep Feature Learning of EEG Signals", arXiv: 1709.08820, Sep. 26, 2017, 10pgs.

Zjajo et al., "Iterative Learning Cascaded Multiclass Kernel Based Support Vector Machine for Neural Spike Data Classification", IEEE, whole document (Year: 2015), 6 pgs.

\* cited by examiner

FIG. 4

SYSTEMS AND METHODS FOR DECODING INTENDED SPEECH FROM NEURONAL ACTIVITY

CROSS-REFERENCE TO RELATED APPLICATIONS

The current application is a continuation of U.S. patent application Ser. No. 16/399,412 entitled "Systems and Methods for Decoding Intended Speech from Neuronal Activity" filed on Apr. 30, 2019 and issued as U.S. Pat. No. 12,008,987 on Jun. 11, 2024, which claims the benefit of and priority under 35 U.S.C. § 119(e) to U.S. Provisional Patent Application No. 62/664,385 entitled "Decoding intended speech from neural activity recorded from inside the brain" filed on Apr. 30, 2018, the entirety of which is incorporated herein by reference in its entirety.

STATEMENT OF FEDERALLY SPONSORED RESEARCH

This invention was made with Government support under contracts DC014034 and NS066311 awarded by the National Institutes of Health. The Government has certain rights in the invention.

FIELD OF THE INVENTION

The present invention generally relates to decoding speech from neuronal activity, and namely to enabling artificial speech to speech-impaired individuals.

BACKGROUND

The language center of the brain refers to areas of the human brain that serve particular functions for speech processing and production. Two traditionally described language centers are Wernicke's area and Broca's area. Wernicke's area is involved in the comprehension of language. Wernicke's area is located in the posterior section of the superior temporal gyrus in usually the left cerebral hemisphere. Broca's area is involved with the physical production of speech (e.g. compiling sounds with syntax). Broca's area is located in the inferior frontal gyrus of the dominant prefrontal cortex. The motor cortex is the region of the cerebral cortex involved in planning control, and execution of voluntary movements. The primary motor cortex is located at Brodmann area 4, with the ventral aspect known to be particularly heavily involved in movement of the speech articulators (jaw, lips, tongue) and a somewhat more dorsal area involved in laryngeal control (vocalization).

SUMMARY OF THE INVENTION

Systems and methods for decoding intended speech from neuronal activity in accordance with embodiments of the invention are illustrated. One embodiment includes a neuronal speech system for decoding intended speech from neuronal signals including a neuronal signal recorder implanted into a human user's brain, including a multielectrode array, controller circuitry, and a communication circuitry capable of transmitting data to a neuronal signal decoder, the neuronal signal decoder located externally from the user's body, including a processor, an input/output interface, and a memory, where the memory contains a neuronal speech application that directs the processor to obtain neuronal signal data from the neuronal signal recorder, where the neuronal signal data describes neuronal activity proximal to the implanted neuronal signal recorder, decode speech features from the neuronal signal data using a neuronal decoding model, construct a speech string from the decoded speech features; and output the constructed speech string via an output device.

In a further embodiment, to decode speech features from the neuronal signal data, the neuronal speech application further directs the processor to use a language model.

In still another embodiment, the language model adapts to the user's speech patterns.

In a still further embodiment, the neuronal decoding model includes a machine learning model.

In yet another embodiment, the machine learning model is a neural network.

In a yet further embodiment, the neuronal signal recorder is implanted below the surface of the user's brain.

In another additional embodiment, the neuronal signal recorder is implanted into the hand/arm region of the motor cortex of the user's brain.

In a further additional embodiment, the multielectrode array is between 1 mm$^2$ and 10 mm$^2$.

In another embodiment again, a given decoded speech feature is selected as probable based on the presence of a previously selected decoded speech feature.

In a further embodiment again, the controller circuitry includes a voltage threshold filtering circuitry, and the voltage threshold filtering circuitry is configured to produce a binary value indicating the presence or absence of an action potential for at least one channel in the multielectrode array based on the recorded voltage on that the at least one channel.

In still yet another embodiment, the voltage threshold filtering circuitry uses a threshold between of −3 and −5 times each electrode's root mean squared voltage value.

In a still yet further embodiment, the controller circuitry is configured to calculate a moving average of a local field potential amplitude or power in a particular frequency band for at least one electrode in the multielectrode array.

In still another additional embodiment, the neuronal signal data includes action potential information and local field potential information from at least one electrode in the multielectrode array.

In a still further additional embodiment, a second neuronal signal recorder is implanted into the user's brain.

In still another embodiment again, the neuronal signal recorder selectively utilizes electrodes in the multielectrode array for recording based on at least one quality metric.

In a still further embodiment again, the output device is a vocalizer.

In yet another additional embodiment, the output device is a text-based messaging system.

In a yet further additional embodiment, the output device is a display device.

In yet another embodiment again, the speech features are speech articulator movements.

In a yet further embodiment again, the speech features are acoustic features.

In another additional embodiment again, a method for decoding intended speech from neuronal signals, including obtaining neuronal signal data from a neuronal signal recorder, where the neuronal signal data describes neuronal activity proximal to the implanted neuronal signal recorder, and the neuronal signal recorder includes a multielectrode array, controller circuitry, and a communication circuitry capable of transmitting data to an external neuronal signal processor, decoding speech features from the neuronal signal data using a neuronal decoding model using a neuronal signal processor, the neuronal signal decoder located externally from the user's body, including a processor, an input/output interface, and a memory, constructing a speech string from the decoded speech features, and outputting the constructed speech string via an output device.

Additional embodiments and features are set forth in part in the description that follows, and in part will become apparent to those skilled in the art upon examination of the specification or may be learned by the practice of the invention. A further understanding of the nature and advantages of the present invention may be realized by reference to the remaining portions of the specification and the drawings, which forms a part of this disclosure.

BRIEF DESCRIPTION OF THE DRAWINGS

The description and claims will be more fully understood with reference to the following figures and data graphs, which are presented as exemplary embodiments of the invention and should not be construed as a complete recitation of the scope of the invention.

DETAILED DESCRIPTION

The human brain is the most complex organ in the human body, and many of its mechanisms remain little understood. While, broadly, different areas and structures within the brain have been strongly linked to various functions, every brain is idiosyncratic and highly plastic. Despite this plasticity, there are many conditions that cannot be quickly or even possibly repaired by the brain restructuring. For example, injuries or diseases that cause paralysis to any of the organs and musculoskeletal structures involved in speech can make communicating extremely difficult or impossible. Systems and methods described herein can record and process neuronal signals in the brain in order to decode intended speech, and vocalize and/or otherwise display the decoded speech to an audience. As such, even those who cannot physically produce sound or write can communicate verbally.

When building a neuronal speech system, it is important to enable high fidelity output. With the goal of efficient communication, high error rates or slow transmission rates can frustrate users and make use of the system less appealing. As such, systems described herein can include specialized recording components as well as positions for recording components to increase efficiency. Neuronal speech processes described herein can decode recorded neuronal signal data into intended speech with a high degree of accuracy. Furthermore, neuronal speech processes can decode intended speech from neuronal signals generated in regions not traditionally associated with producing auditory speech, e.g. from other regions of the motor cortex. The ability to utilize these signals creates the opportunity for integration with other brain-computer interface (BCI) systems that are used for other purposes. For example, prosthetic control systems may utilize neuronal signals generated in the dorsal hand/arm region of the motor cortex, and therefore preferentially implant neuronal recorders in that region. Neuronal speech systems described herein can be integrated into such prosthetic control systems (or other BCI systems) without the need for additional implants.

Known methods of capturing and decoding neural signals generally involve the use of relatively large electrocorticography (ECoG) electrode grids that are placed under the skull over a wide area of the surface of the brain. While speech has been captured using this method, the electrode grids require relatively large craniotomies, but do not provide a high spatial resolution on neuronal signals in the brain. Because each electrode picks up the electrical fields generated by the firing of tens if not hundreds of thousands of neurons, the received signal is noisy and less specific than recording all of (or even a sufficient fraction of) these neurons' individual activities. Further, known processes have been tailored to this type of data. In many embodiments, systems and methods described herein utilize neuronal signal recorders that use small, multielectrode arrays (e.g. on the order of hundreds to thousands of densely packed electrode recording sites) that are implanted inside of the brain structure in one or more specific region(s). Due to the reduced size of neuronal signal recorder, smaller incisions can be used to implant them. Additionally, in contrast to the conventional ECoG systems where the electrodes are placed on the exterior of the brain, neuronal signal recorders are able to be implanted deeper into the tissue of the brain in order to better capture neuronal signals of interest. Further, in numerous embodiments, neuronal signal recorders can filter recorded neuronal signals in unconventional ways discussed below to decrease the amount of data, and therefore the amount of power and/or time required to transmit said data, to external neuronal signal decoders. This reduction in data and power demands facilitates making these systems fully implantable with wireless data telemetry and power transmission, thus removing the need to have external wires going through the skin. Neuronal speech systems for decoding intended speech from neuronal signals are discussed in further detail below.

Neuronal Speech Systems

The brain is extremely delicate and any physical manipulation of its tissues carry risk to the patient. As such, neuronal speech systems can be designed in such a way as to reduce the size of implants and/or amount of manipulation required to place implants. Modern research has generally utilized large ECoG electrode grids (e.g. those used for the treatment of epilepsy). However, while neuronal speech systems can function using larger electrode grids, in many embodiments, neuronal speech systems utilize small, multielectrode arrays between approximately 1 mm$^2$ and 10 mm$^2$. Using small implants can enable higher quality readings with high spatial resolution, as well as, depending on the placement, reduce the invasiveness of the implantation process.

Figure 1:
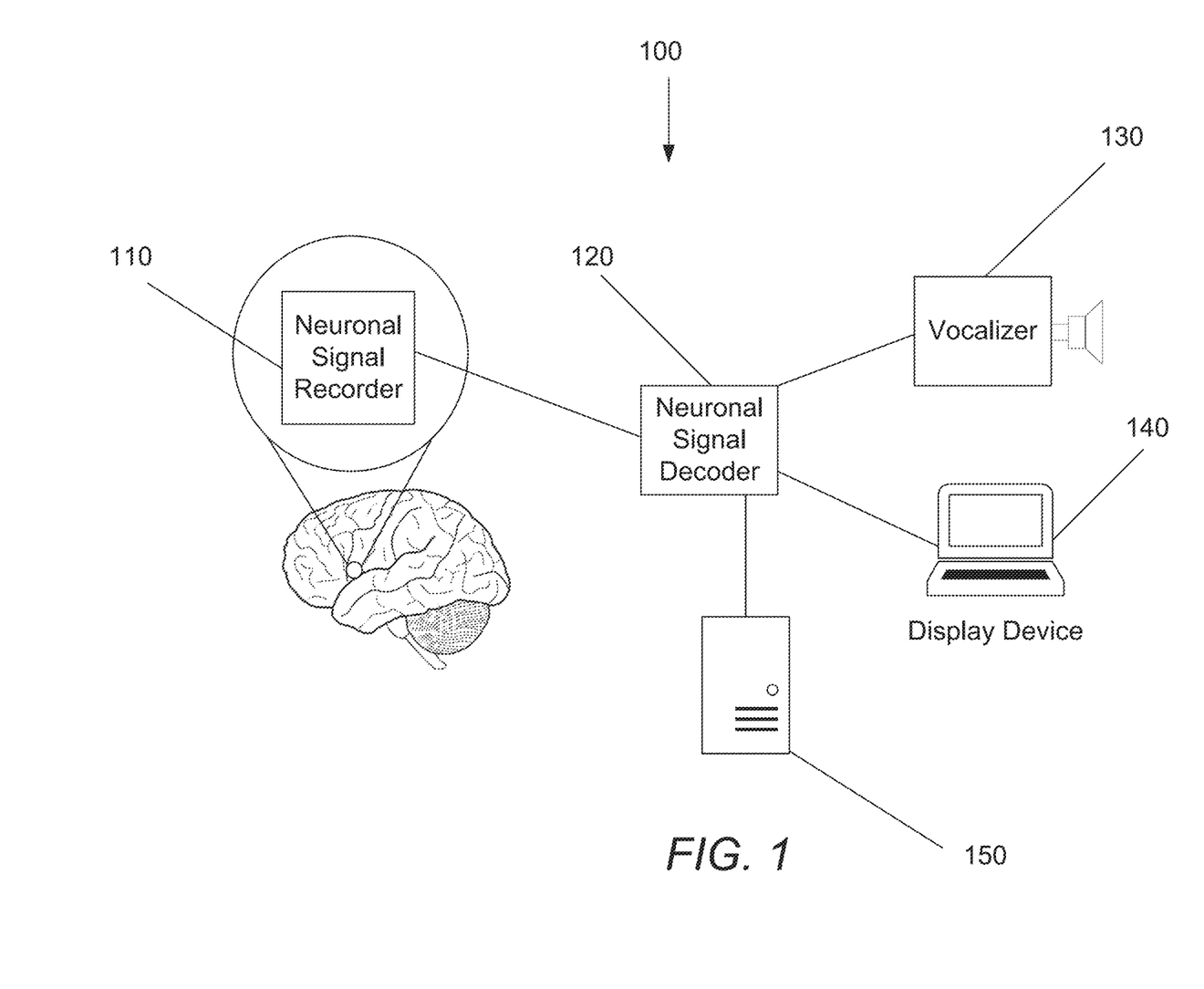
FIG. 1 conceptually illustrates a neuronal speech system in accordance with an embodiment of the invention.

Turning now to FIG. 1, a neuronal speech system in accordance with an embodiment of the invention is illustrated. Neuronal speech system 100 includes a neuronal signal recorder 110. Neuronal signal recorders record electrical activity (e.g. action potentials, also known as "spikes", and/or local field potentials) in the brain as neuronal signal data. Neuronal signal recorder 110 is implanted into the brain of a patient. In many embodiments, the neuronal signal recorder is implanted at the hand/arm area of the motor cortex. However, in numerous embodiments, the neuronal signal recorder is implanted at Broca's area, Wernicke's area, face areas of (ventral) motor cortex, or elsewhere in the brain. In many embodiments, more than one neuronal signal recorder can be implanted into a brain.

Neuronal signal recorders utilize dense electrode arrays to collect neuronal signals describing the firing of neurons near electrodes in the array. In numerous embodiments, neuronal signal recorders further include controller circuitry enabling the pre-processing of recorded signals. For example, as opposed to the more conventional full-bandwidth methodology to allow subsequent "spike sorting" (assigning action potentials to putative individual neurons from which they originate), a "voltage threshold filtering" circuit can be implemented (e.g. as part of the controller circuitry and/or as its own module). Voltage threshold filtering is discussed further below with respect to FIG. 2. Neuronal signal recorders further include communication circuitry that can be used to transmit data to external devices. In some embodiments, the communication circuitry includes a wired connection from inside the user's skull to outside of the user via a physical port in the skin and/or skull. However, in numerous embodiments, pre-processing of the recorded data reduces the amount of data needed to be transmitted to a small enough size to be able to be transmitted over a low power wireless connection. For example, via Near Field Communication (NFC), magnetic communication techniques, electromagnetic communication, or optical communication techniques can be utilized as appropriate to the requirements of specific applications of embodiments of the invention. However, in some embodiments, a wired connection can be utilized instead of, or as well as, a wireless connection. Communication circuitry can include, but is not limited to, transmitters, receivers, transceivers, antennas, coils, and/or any other circuitry utilized for the transmission and/or reception of data from an external device as appropriate to the requirements of specific applications of embodiments of the invention.

Neuronal speech system 100 further includes a neuronal signal decoder 120. Neuronal signal decoders receive neuronal signal data from neuronal signal recorders and decode intended speech from the neuronal signal data. Neuronal processors can provide decoded intended speech to various output devices in order to convey the intended speech of the user. Output devices can include, but are not limited to, vocalizers 130, display devices 140, and/or computer systems 150. Vocalizers utilize text-to-speech processes to synthesize and output sound that mimics a human voice speaking the particular input text. In many embodiments, bespoke vocalizers can be used based on the user's own pre-recorded speech. Display devices utilize screens to display text in a visual manner. Display devices can be any type of device capable of displaying text, such as, but not limited to, smart phones, personal computers, tablet computers, televisions, monitors, e-ink screens, and/or any other display as appropriate to the requirements of specific applications of embodiments of the invention. Computer systems utilized as output devices can receive intended speech and use it for any of a variety of applications, including, but not limited to, word processors, messaging systems, electronic mail systems, or any other computer application as appropriate to the requirements of specific applications of embodiments of the invention. In many embodiments, neuronal speech systems include more than one output device. Output devices can be connected to neuronal signal decoders via a communications link. Communications links can be wired or wireless. In numerous embodiments, an output device is connected to the neuronal signal decoder via a network (e.g. the Internet, a cellular data network, a local area network, etc.) to enable distant communication. In a variety of embodiments, neuronal signal decoders include an integrated output device.

While a specific system architecture for neuronal speech systems is illustrated in FIG. 1, any number of system architectures, including, but not limited to, those that integrated into wearable devices, prosthetics, and/or mobility devices in order to reduce burden on the user can be utilized as appropriate to the requirements of specific applications of embodiments of the invention. A discussion of neuronal signal decoders can be found below.

Neuronal Signal Decoders

Figure 2:
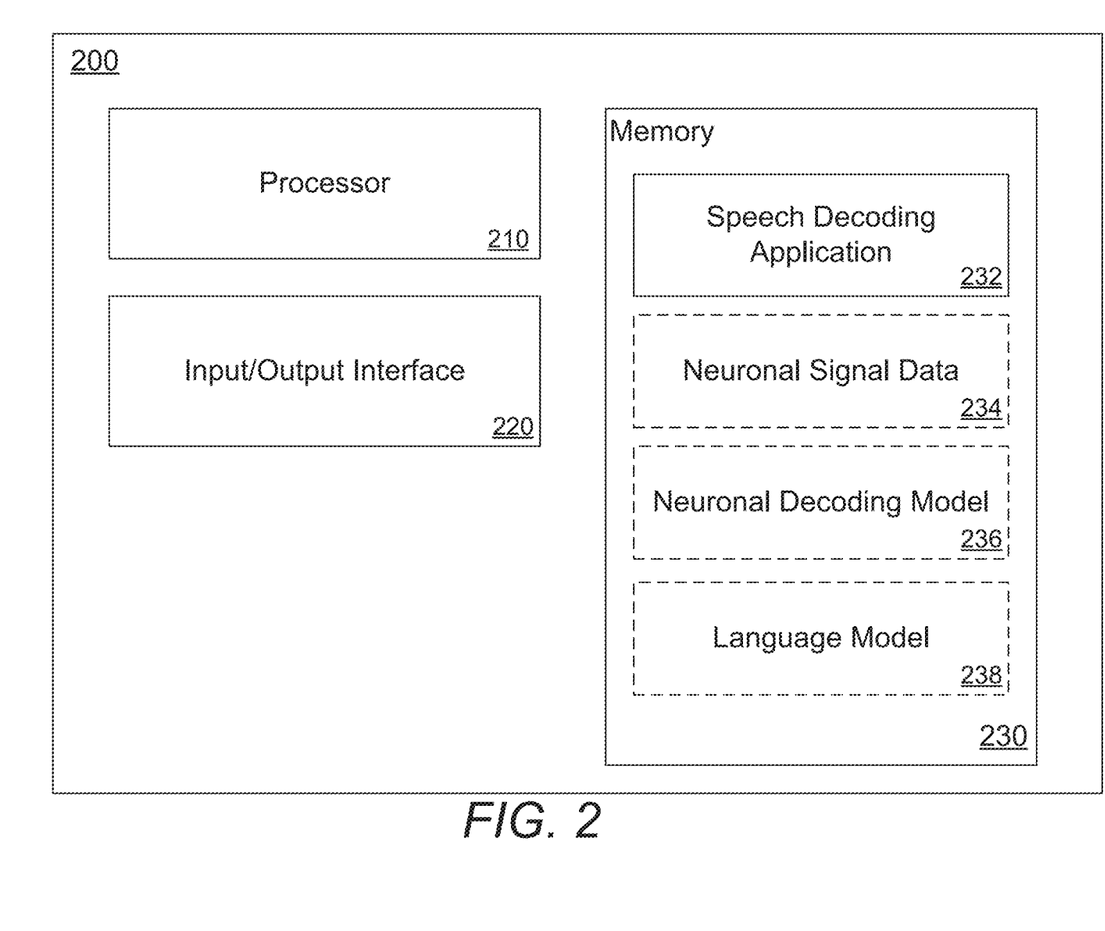
FIG. 2 is a block diagram conceptually illustrating a neuronal signal decoder in accordance with an embodiment of the invention.

Neuronal signal decoders obtain neuronal signal data from neuronal signal recorders and decode intended speech from the obtained data. In numerous embodiments, neuronal signal decoders are located externally from the user, as heat generated through processing can damage tissue. An external neuronal signal decoder can therefore be more powerful, flexible, and upgradable than an implanted component. Turning now to FIG. 2, a neuronal signal decoder in accordance with an embodiment of the invention is illustrated.

Neuronal signal decoder 200 includes a processor 210. Processors can be any number of different logic processing units, including, but not limited to, central processing units (CPUs), graphics processing units (GPUs), field-programmable gate-arrays (FPGAs), application specific integrated circuits (ASICs), and/or any other logic processing unit as appropriate to the requirements of specific applications of embodiments of the invention. Neuronal signal decoder 200 further includes an input/output interface 220. Input/output interfaces can be used to obtain neuronal signal data from neuronal signal recorders as well as transmit decoded speech to output devices. In numerous embodiments, the input/output interface is used to communicate information and/or commands back to the neuronal signal recorder in order to adjust that component's parameters, such as, but not limited to, the voltage threshold for spike detection, in order to improve the performance of the overall system. Input/output interfaces can utilize more than one communications method such that communication with both a neuronal signal decoder and an output device is possible. The communications method utilized can be either wired or wireless. For example, a neuronal signal decoder can communicate wirelessly with a neuronal signal recorder while being hardwired to an output device. In some embodiments, the input/output interface connects to a secondary connection device in order to facilitate communication between components in the neuronal speech system.

Neuronal signal decoder 200 further includes a memory 230. Memory can be implemented using non-volatile storage media, volatile storage media, or a mix thereof. Memory 230 contains a speech decoding application 232. Speech decoding applications can direct the processor to perform neuronal speech processes similar to those discussed below. In numerous embodiments, memory 230 further contains neuronal signal data 234 obtained from the neuronal signal recorder, the neuronal decoding model 236, and a language model 238.

In many embodiments, neuronal signal data describes the voltage values recorded at each electrode in the electrode array. In various embodiments, neuronal signal data describes features extracted from the neuronal signal recorded from each electrode in the array. However, many different forms of neuronal signal data, such as those that aggregate information, include only specific electrode recordings, or otherwise describe action potentials can be used as appropriate to the requirements of specific applications of embodiments of the invention.

Neuronal decoding models describe conversions from activation patterns in neuronal signals to speech information. For example, neuronal decoding models can map a specific activation pattern to a specific phoneme, syllable, word, phrase, or any other linguistic unit as appropriate to the requirements of specific applications of embodiments of the invention. In numerous embodiments, the neuronal decoding model can map neuronal activity to attempted movements of the speech articulators, from which sound can be synthesized. Neuronal decoding models and their generation are discussed in further detail below with respect to FIG. 4.

In a variety of embodiments, language models provide statistical predictions as to what a given speech feature will be given previously decoded speech features to neuronal decoding models. In many embodiments, language models are default statistical probabilities for word order in a given language. In a variety of embodiments, language models are adaptive, i.e. probabilities can be updated based on the speech patterns of the user. While a specific neuronal signal decoder is discussed above with respect to FIG. 2, any number of different architectures can be utilized, such as those with additional or modified components, as appropriate to the requirements of specific applications of embodiments of the invention. Neuronal speech processes are discussed below.

Neuronal Speech Processes

Neuronal speech processes convert neuronal signals into the intended speech of the user from which the neuronal signals were obtained. The human brain goes through multiple steps in order to conceptualize, formulate, and articulate speech. The conceptualization step involves linking concepts to words which will be expressed. The formulation step includes grammatical encoding, morpho-phonological encoding, and phonetic encoding in order to construct a series of articulatory gestures that will produce the correct sound wave associated with the speech. At the grammatical encoding stage, the correct lemma is selected, which then triggers an appropriate syntactic frame. The morpho-phonological encoding stage breaks down the words into individual syllables. The phonetic encoding stage involves selection of the appropriate phonemes. Finally, the articulation step involves the execution of the appropriate physical movements required to enact the production of the sound wave in accordance with the order of the phonemes.

Each one of these steps occurs across multiple areas of the brain. While research into the function of the many neuronal circuits in the brain is ongoing, Wernicke's area is generally involved with the conceptualization step of speech. Broca's area is generally understood to be involved in the formulation step. The motor cortex is generally understood to be involved in the articulation step, and specifically, the areas of the motor cortex involved in controlling the lungs, glottis, larynx, tongue, lips, jaw, and other parts of the vocal apparatus ('speech articulators'). Neuronal speech processes can utilize neuronal signals from any of these areas of the brain. However, in many embodiments, neuronal speech processes utilize neuronal signals from the arm/hand region of the motor cortex, which is located dorsally with respect to the portion of the motor cortex involved with the vocal apparatus and is not traditionally associated with producing speech.

Figure 3:
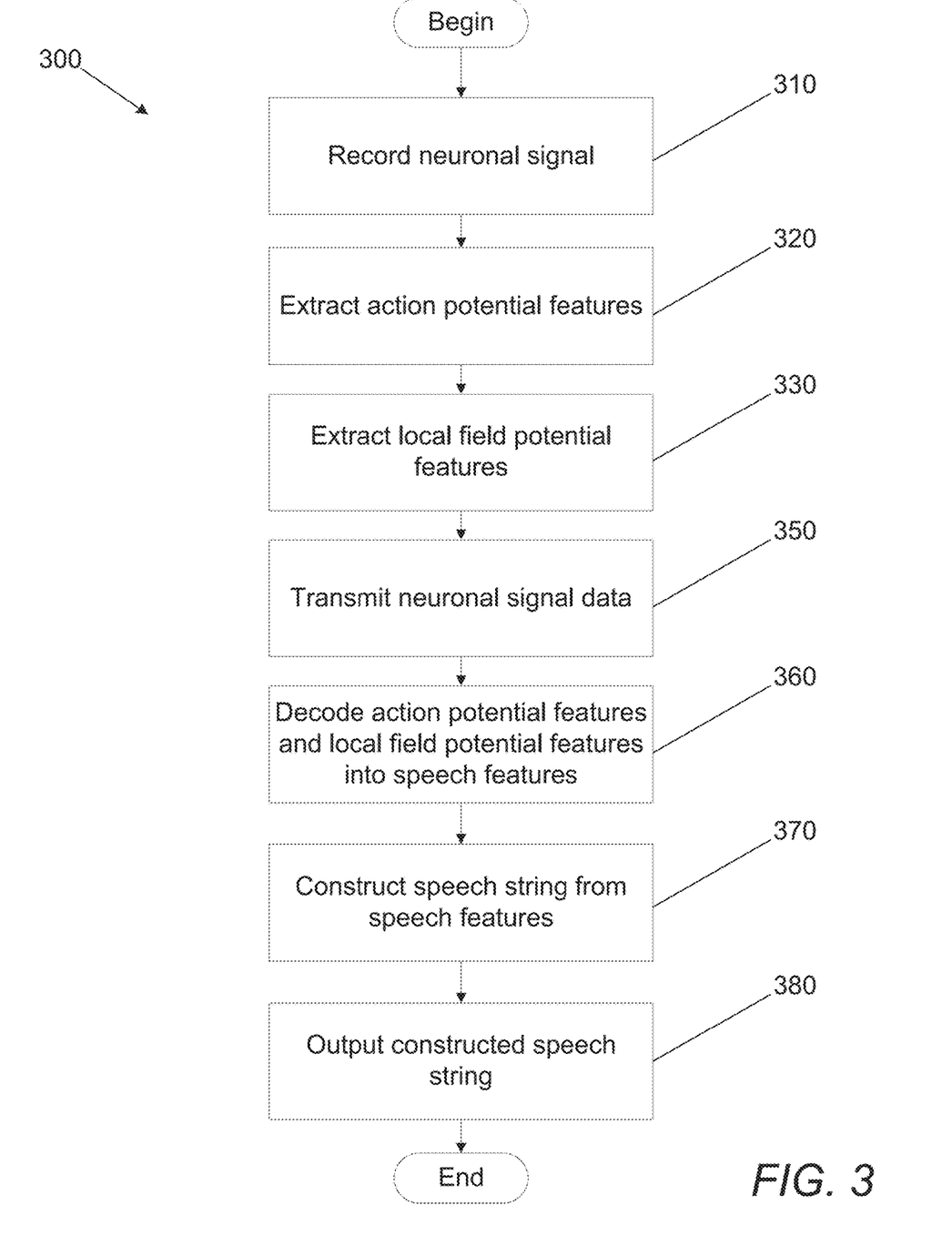
FIG. 3 is a flow chart illustrating a neuronal speech process for constructing speech strings from speech features in accordance with an embodiment of the invention.

Turning now to FIG. 3, a process for decoding and outputting intended speech from neuronal signals in accordance with an embodiment of the invention is illustrated. Process 300 includes recording (310) a neuronal signal. In numerous embodiments, neuronal signal data is obtained using a neuronal signal recorder. For each recording site in the electrode array of the neuronal signal recorder (i.e., each "channel"), a voltage can be measured. In many embodiments, the voltage values are approximately 16 bits, with a resolution of approximately 0.25 microvolts per bit. However, any number of different resolutions and sample sizes can be used as appropriate to the requirements of specific applications of embodiments of the invention. In a variety of embodiments, electrodes that are determined to be producing signal of insufficient quality (due to artifact, noise, irrelevance, etc.) can be selectively turned off and not used for recording. This can reduce power and communication bandwidth demands on the system.

Process 300 further includes extracting (320) action potential features from the neuronal signal. Action potential features are signals from one or a small number of individual neurons near a given recording electrode. Neuronal signal recorders, as noted above, can contain circuitry enabling the pre-processing of neuronal signals recorded via electrodes. In many embodiments, neuronal signals are measured with a relatively high degree of sensitivity. Consequently, the size of the data required for each sample (e.g. the storage capacity needed as measured in bits) is often quite high. For example, a 96-electrode array sampling at 30 kHz, where each sample is a 16 bit value would produce approximately 5.8 megabytes per second of data. Conventionally, this large amount of data would be processed externally via a process referred to as "spike sorting." Spike sorting is a process by which each action potential recorded is assigned to an individual neuron. Manual spike sorting is very complex and can take hours. Automatic spike sporting methods have proven to be computationally intensive, and no ground truth data is available for validation. Importantly, spike sorting may not be necessary to decode signals from the brain.

In contrast, extraction of action potential features can occur on the implanted neuronal signal recorder. In many embodiments, voltage threshold filtering is used to reduce the amount of data sent. Voltage threshold filtering can, but need not, first involve common average referencing the voltage measurements within a given electrode array. The mean-subtracted voltages are then band-pass filtering processing between approximately 0.3 Hz and 7.5 kHz followed by a high pass filtering above 250 Hz. Next, a voltage threshold for each electrode is instantiated producing a single bit value that can be used to describe whether the threshold was hit at the particular sample. In some embodiments, the threshold voltage is $-3.5\times$ each electrode's root mean squared voltage value. However, any number of different thresholds can be used, including, but not limited to threshold voltages between approximately $-3\times$ to $-5\times$ root mean squared voltage, as appropriate to the requirements of specific applications of embodiments of the invention. Consequently, when utilizing voltage threshold filtering, the 96-electrode array in the example discussed above would merely need to transmit approximately 0.36 megabytes per second. The resulting action potential feature is then a binary value of whether or not an action potential occurred at each electrode in the array.

Process 300 further includes extracting (330) local field potential (LFP) features from the neuronal signal. Similar to the extraction of action potential features, extraction of LFP features can be performed by neuronal signal recorders. In contrast to action potential features which describe the firing of a single or small amount of neurons, LFP features describe the aggregate neuronal activity in a large area around the particular electrode (both firing of local neurons' action potentials, as well as synaptic currents due to action potentials arriving to this region). In numerous embodiments, LFP features are used to compensate for an insufficient amount of electrodes recording action potentials in the electrode array, and/or to improve performance by decoding an additional signal source. As more electrodes are added to the array (generally resulting in an increase in size of the array), the importance of extracting LFP features is diminished. Local field potential features can be extracted by running a recorded neuronal signal through a band-pass filter between approximately 125 Hz and 5000 Hz. This "high gamma" band can be used to increase accuracy by supplementing action potential features. In order to reduce bandwidth required to transmit local field potential features, average power in the frequency band of interest, or its analytic envelope, or other aggregating measurements, can be taken over a predetermined time window using the neuronal signal recorder, which are then transmitted instead of each sample. For example, in numerous embodiments, the average power in a sliding time window (for example, a 50 ms window) updated every millisecond is calculated, resulting in a much smaller amount of data that would need to be transmitted compared to the raw data produced by a 30000 Hz sampling rate.

The action potential features and local field potential features are packaged as neuronal signal data and transmitted (350) from the implanted neuronal signal recorder to the neuronal signal decoder. In numerous embodiments, the extraction of features by the implanted neuronal signal recorder enables wireless transmission from inside of the brain to the external neuronal signal decoder. The action potential features and local field potential features are decoded (360) into speech features. In many embodiments, a decoder based on a trained neuronal decoding model is used to convert the action potential features and local field potential features into a series of speech features. This neural to speech decoding can be improved by the further inclusion of a language model, which adjusts the prior probability of different speech features based on the recent history of the system's outfit and the known statistical properties of the language being spoken, and, in some embodiments, historical patterns of speech specific to the user. For example, a neuronal decoder model can be used to produce a sequence of speech features which may contain errors or incomplete sounds and/or phrases. A language model can be used to correct errors in the sequence of speech features. In many embodiments, this error correction occurs in parallel with the production of the speech string so that accurate strings can be used in further decoding of the neuronal signal data by the neuronal decoder model.

Different types of machine learning models can be used as the foundation of neuronal decoding models and language models appropriate to the requirements of specific applications of embodiments of the invention. Two main types of machine learning model are classification-based models and regression-based models. In a classification-based system, the input features are used to predict which of a finite set of known linguistic units (also referred to as "text-based speech features") the user is trying to make (e.g. which phoneme, which word from a dictionary, which pre-set phrase). In contrast, a regression-based system regresses the input features against acoustic features (e.g. pitch, amplitude, etc.) and/or physical movements (e.g. velocity of the tongue and lips, etc., also referred to as "articulation features") which can be used to generate a continuous range of sound-based speech features. In many embodiments, predictive language models (where previous outputs change the prior probability distribution of the possible current output) can be integrated into the decoder in order to enhance accuracy. In some embodiments, language models are able to update the probability of a particular speech feature for a particular set of input features based on prior or subsequent sets of input features in the time series with respect to the particular speech feature.

Action potential features and local field potentials can be represented as a time-series of values. In many embodiments, the decoder bins these input features by time, and the values in the bins can be concatenated as a single input vector (e.g. as a single data structure containing both the action potential features and the local field potential features of a particular time window. In numerous embodiments, non-overlapping 100 ms bins are utilized. However, the size of the bins can vary depending upon the training protocol utilized for the neuronal decoding model. Binning neural features can reduce the data and power demands associated with transmission of these signals from outside the brain; for example, if the action potential feature is the presence or absence of spike(s) in a 5 ms bin (rather than in a e.g., 1 ms sample), then the transmission data requirement is reduced 5-fold with only minimal loss of information (since in practice neurons rarely fire multiple action potentials in such a small window of time).

Similarly, speech features can be determined by how the machine learning model was trained. In numerous embodiments, speech features are phonemes. In a variety of embodiments, speech features are a sound wave. However, speech features can be words or phrases selected from a pre-determined dictionary. Speech features are constructed (370) into a "speech string" by concatenating sequential output speech features. In numerous embodiments, a secondary predictive model can be used to convert phonemes and/or sound waves in the speech string into specific words. This speech string is then output (380) via a display device. This output can be display of the speech string text and/or the vocalization of the speech string via a speaker. As noted above, in many embodiments, the specific operation of a decoder is dependent upon how it was trained. A discussion of how to create and train machine learning models for use in decoders is discussed below with respect to FIG. 4.

Constructing Neuronal Decoding Models

While brain structure is typically conserved across all humans, each person has idiosyncrasies that frustrate a generalized neuronal decoding model. Furthermore, which specific neurons are recorded will depend on the precise location of each individual electrode implant. In order to address these idiosyncrasies, neuronal decoding models can be constructed as a machine learning model that is trained based on data obtained from the individual user, typically in a clinical setting. As noted above, there are many different approaches to constructing neuronal decoding models. In many embodiments, the type of neuronal decoding model is influenced by the location of the implanted neuronal signal recorder. In turn, the location of the implanted neuronal signal recorder may be influenced by the presence of tissue damage in the brain itself. Depending on the region of implantation, signals corresponding to different stages of speech (conceptualization, formulation, and articulation) may be more cleanly identified. Furthermore, depending on a number of factors, including, but not limited to, implantation location, preferred output device, signal quality, and signal clarity, the neuronal decoding model can be trained to output any of a number of different types of speech features. In many embodiments, many different neuronal decoding models can be trained, each utilizing a different target speech feature in order to determine the model that produces the highest accuracy.

Figure 4:
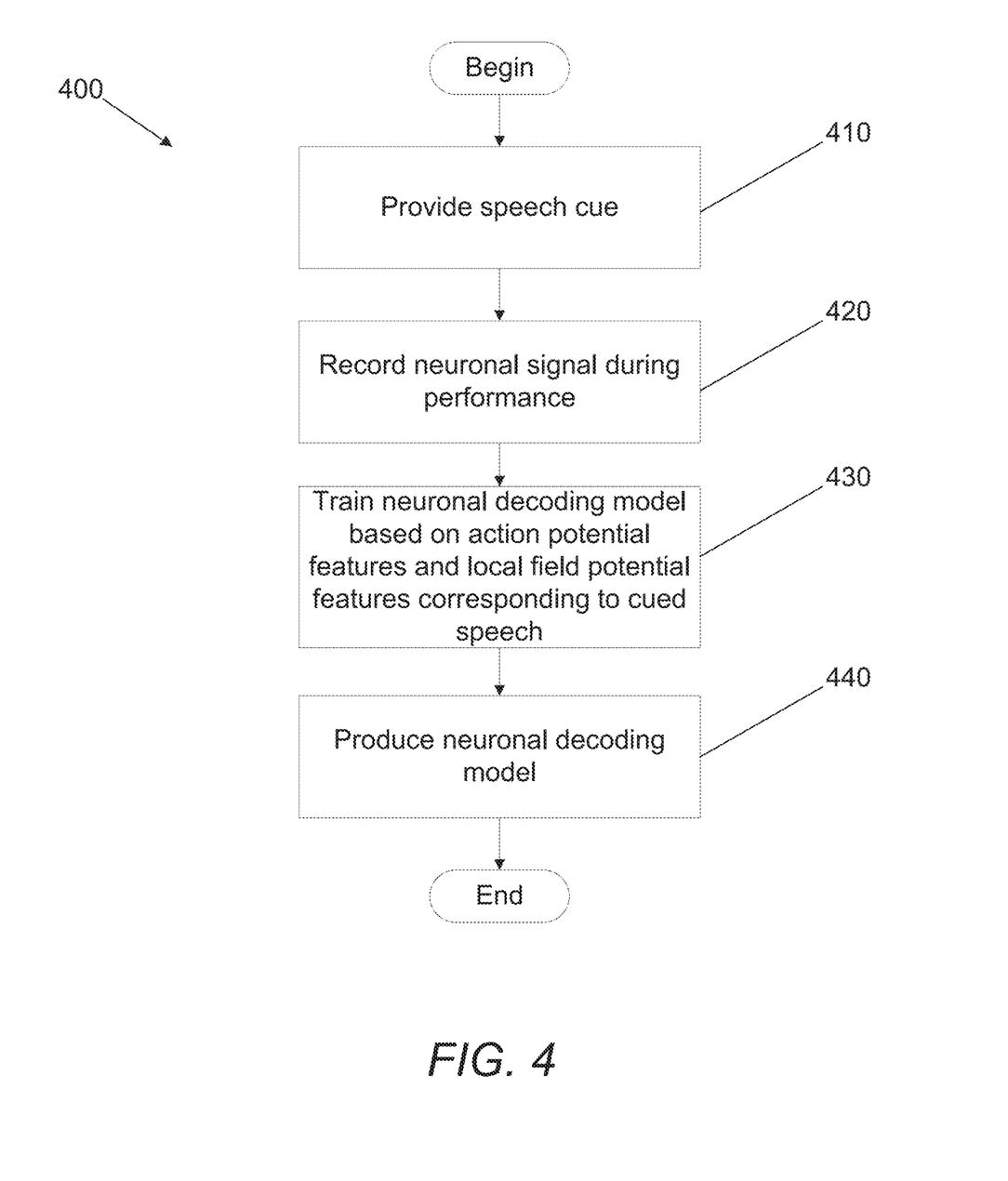
FIG. 4 is a flow chart illustrating a neuronal speech process for generating neuronal decoding models in accordance with an embodiment of the invention.

Turning now to FIG. 4, a neuronal speech process for constructing a neuronal decoding model in accordance with an embodiment of the invention is illustrated. Process 400 includes providing (410) a speech cue to a user who has an implanted neuronal signal decoder. The provided speech cue can be an indication to speak a word, a sound, or a phrase, make a mouth or lip or tongue or larynx movement, and/or an indication to intend to vocalize a word, a sound, or a phrase. In some embodiments, depending on the needs of the user, the speech cue can be an indication to perform an intentional movement not traditionally associated with speech, e.g. moving a finger, an arm, a toe, etc. The corresponding neuronal signal associated with the user's response to the speech cue is recorded (420) and processed similarly to as described above to extract action potential features and local field potential features.

A neuronal decoding model can then be trained (430) based on the action potential features, local field potential features, and cued speech. In many embodiments, the prediction phase involves the training of a machine learning model. In some embodiments, the machine learning model is a support vector machine (SVM) to associate particular neuronal signals with a particular speech feature. In a variety of embodiments, a neural network architecture is used as the machine learning model. In some embodiments, multiple different machine learning models are utilized in tandem. For example, a first neural network can be used to decode the neuronal signal data into phonemes or speech articulator movements, and a second neural network can be used to convert the phonemes or speech articulator movements into predicted words. However, any number of different architectures can be used as appropriate to the requirements of specific applications of embodiments of the invention.

In a variety of embodiments, more than one training phase can be implemented. For example, an "open-loop" phase may precede a "closed-loop" phase. An open-loop phase involves calibration based the prompted speech. The neuronal activity at the time of the user's prompted action is assumed to correspond to the cue. In some embodiments, the detection of a neuronal condition-invariant signal is used as a trigger to begin defining the region of interest in the neuronal signal. The decoder trained via the open loop method can then be used to produce cued speech in a second around of training. For example, the user can be again cued to attempt to produce a particular sound/word/phrase, which can then presented to the user in real-time (for example, as sound or as on-screen text), which produces a set of closed loop training data. This iterative process can improve the neuronal decoding model and account for neuronal activity changes between open-loop contexts (when the user has no feedback about how the speech prosthesis is functioning) and closed-loop context (when the user is seeing or hearing the output of the device shortly after attempting a particular speech action). Weights (parameters in the algorithm) in the neuronal decoding model can be updated based on the closed loop training data such that the output of the decoder would have been closer to the cued speech.

This dual training method can help mitigate differences that can arise from attempting to say something without a neuronal speech system and a directed attempt to utilize the neuronal speech system. Closed loop training can be iteratively performed in order to further increase accuracy. Further, closed loop training can be performed whenever degradation of the language model is detected (e.g. due to neurological changes in the user). This can be triggered automatically (for example, if the output phrases do not sufficiently adhere to known statistical language models for some period of time), or manually by the user or trusted other individuals who have the permission to initiate a calibration routine in the speech prosthesis system.

Once training is complete, the final neuronal decoding model is produced (440) and integrated into the neuronal speech processor. By using a trained neuronal decoding model based on the individual user, a higher degree of accuracy can be achieved. In many embodiments, the neuronal decoding model can be replaced or updated in order to adjust for an increase in user expertise with the neuronal speech system, a degradation or other change in the user's condition, or for any of a number of other reasons as appropriate to the requirements of specific applications of embodiments of the invention. For example, an introductory neuronal decoding model may be designed to function with a limited set of speech features, e.g. a dictionary of key phrases (e.g. yes, no, hungry, thirsty, tired, good, bad, hurt, etc.). The vocabulary can be expanded via retraining or regeneration of the neuronal decoding model. In some embodiments, multiple language models may be used and swapped between. For example, a limited dictionary may have higher accuracy due to the limited feature space. However, a larger dictionary or a phoneme-based neuronal decoder model could be utilized when more complex communication is desired, sometimes at the expense of accuracy. Similar results can be achieved by mixing different types of speech features in the same language model (e.g. a mix of phonemes and words, etc.). For example, specific, often used phrases can be incorporated as part of the neuronal decoding model as well as a dictionary of words. As such, neuronal decoding models can be tailored and refactored to the individual user's needs at any given time.

Although specific methods of decoding intended speech from neuronal signals are discussed above, many different decoding methods, such as, but not limited to, those utilizing different machine learning algorithms, can be implemented in accordance with many different embodiments of the invention. For example, with respect to processes described herein, the ordering of certain steps can be rearranged, performed in parallel, and/or selectively be not performed in accordance with various embodiments of the invention. It is therefore to be understood that the present invention may be practiced in ways other than specifically described, without departing from the scope and spirit of the present invention. Thus, embodiments of the present invention should be considered in all respects as illustrative and not restrictive. Accordingly, the scope of the invention should be determined not by the embodiments illustrated, but by the appended claims and their equivalents.

What is claimed is:

1. A brain-machine interface for speech, comprising:
a processor; and
a memory, the memory containing a speech decoding application that configures the processor to:
  initialize an open-loop training phase, where the processor is configured to:
    provide a prompt to the user to attempt to speak a given phrase; and
    obtain open-loop neuronal signal data from an array of microelectrodes configured to be implanted into human user's brain, where the open-loop neuronal signal data is recorded during the providing of the prompt; and train a neuronal decoding model and a language model to decode speech features from neuronal signal data using the provided prompt and the open-loop neuronal signal data, where the neuronal decoding model is configured to generate speech feature probabilities from neuronal signal data, and the language model is configured to adjust prior probabilities of different speech features based on previous speech feature probabilities produced by the neuronal decoding model;

obtain operational neuronal signal data from the array of microelectrodes, where the operational neuronal signal data is recorded outside of a training phase;

decode operational speech features from the operational neuronal signal data using the neuronal decoding model and the language model;

construct an operational speech string from the decoded operational speech features;

determine if the language model has degraded based on adherence to a statistical language model;

in response to a determination of degradation, initialize a closed-loop training phase, where the processor is configured to:

provide a second prompt to the user to attempt to speak a given phrase;

obtain closed-loop neuronal signal data from the array of microelectrodes, where the closed-loop neuronal signal data is recorded during the providing of the prompt;

decode speech features from the closed-loop neuronal signal data using the neuronal decoding model and the language model;

construct a speech string from the decoded speech features;

provide the speech string to the user; and when the speech string does not match the second prompt, retrain the language model using the closed-loop neuronal signal data and the second prompt.

2. The brain-machine interface of claim 1, where in order to provide the speech string, the speech decoding application further configures the processor to playback the speech string.

3. The brain-machine interface of claim 1, where in order to provide the speech string, the speech decoding application further configures the processor to display the speech string via a text-based messaging system.

4. The brain-machine interface of claim 1, wherein the speech features are phonemes.

5. The brain-machine interface of claim 1, wherein the speech features are articulation features.

6. The brain-machine interface of claim 1, further comprising:

the microelectrode array, where each microelectrode in the array of microelectrodes provides at least one channel for measurement of neuronal activity;

a voltage threshold filtering circuitry configured to:
apply a band-pass filter to each measurement; and
apply a voltage threshold to the band-pass filtered measurements of between −3× and −5× of root mean squared voltage of the at least one channel to produce a binary value indicating the presence or absence of an action potential (AP) for the at least one channel; and a controller circuitry, where to produce neuronal signal data, the controller circuitry is configured to:

record local field potentials (LFPs) and APs from each microelectrode in the array of microelectrodes via the voltage threshold filtering circuitry; and bin features describing the LFPs and APs from each microelectrode in the array of microelectrodes in a plurality of bins, where each covers a time window between 5 ms and 100 ms.

7. The brain-machine interface of claim 1, wherein the neuronal decoding model is a machine learning model.

8. The brain-machine interface of claim 7, wherein the machine learning model is a support vector machine.

9. The brain-machine interface of claim 1, wherein the speech decoding application further configures the processor to swap the language model for a different language model.

10. The brain-machine interface of claim 1, wherein the language model is a machine learning model.

11. A method for speech decoding using a brain-machine interface, comprising:

initializing an open-loop training phase, comprising:
providing a prompt to the user to attempt to speak a given phrase; and
obtaining open-loop neuronal signal data from an array of microelectrodes configured to be implanted into human user's brain, where the open-loop neuronal signal data is recorded during the providing of the prompt; and training a neuronal decoding model and a language model to decode speech features from neuronal signal data using the provided prompt and the open-loop neuronal signal data, where the neuronal decoding model is configured to generate speech feature probabilities from neuronal signal data, and the language model is configured to adjust prior probabilities of different speech features based on previous speech feature probabilities produced by the neuronal decoding model;

obtaining operational neuronal signal data from the array of microelectrodes, where the operational neuronal signal data is recorded outside of a training phase;

decoding operational speech features from the operational neuronal signal data using the neuronal decoding model and the language model;

constructing an operational speech string from the decoded operational speech features;

determining if the language model has degraded based on adherence to a statistical language model;

in response to a determination of degradation, initializing a closed-loop training phase, comprising:
providing a second prompt to the user to attempt to speak a given phrase;
obtaining closed-loop neuronal signal data from the array of microelectrodes, where the closed-loop neuronal signal data is recorded during the providing of the prompt;
decoding speech features from the closed-loop neuronal signal data using the neuronal decoding model and the language model;
constructing a speech string from the decoded speech features;
providing the speech string to the user; and
when the speech string does not match the second prompt, retraining the language model using the closed-loop neuronal signal data and the second prompt.

12. The speech decoding method of claim 11, wherein providing the speech string comprises playing back the speech string.

13. The speech decoding method of claim 11, wherein providing the speech string comprises displaying the speech string via a text-based messaging system.

14. The speech decoding method of claim 11, wherein the speech features are phonemes.

15. The speech decoding method of claim 11, wherein the speech features are articulation features.

16. The speech decoding method of claim 11, wherein each microelectrode in the array of microelectrodes provides at least one channel for measurement of neuronal activity; and the method further comprises:
    applying a band-pass filter to each measurement;
    applying a voltage threshold to the band-pass filtered measurements of between −3× and −5× of root mean squared voltage of the at least one channel to produce a binary value indicating the presence or absence of an action potential (AP) for the at least one channel;
    recording local field potentials (LFPs) and APs from each microelectrode in the array of microelectrodes; and
    binning features describing the LFPs and APs from each microelectrode in the array of microelectrodes in a plurality of bins, where each covers a time window between 5 ms and 100 ms, in order to produce neuronal signal data.

17. The speech decoding method of claim 11, wherein the neuronal decoding model is a machine learning model.

18. The speech decoding method of claim 17, wherein the machine learning model is a support vector machine.

19. The speech decoding method of claim 11, further comprising swapping the language model for a different language model.

20. The speech decoding method of claim 11, wherein the language model is a machine learning model.

* * * * *